US012638414B2

(12) United States Patent
Kern, III et al.

(10) Patent No.: US 12,638,414 B2
(45) Date of Patent: May 26, 2026

(54) **DEVICE, PROCEDURE AND SYSTEM FOR DETECTING BACTERIAL PATHOGENS INCLUDING METHICILLIN-RESISTANT *STAPHYLOCOCCUS AUREUS* OR CLOSTRIDIUM DIFFICILE**

(71) Applicants:Clifford H. Kern, III, Metairie, LA (US); Edward M. Yokley, Anderson, SC (US); William Tison Wyatt, Marshall, NC (US); Morton Greene, Las Vegas, NV (US)

(72) Inventors: Clifford H. Kern, III, Metairie, LA (US); Edward M. Yokley, Anderson, SC (US); William Tison Wyatt, Marshall, NC (US); Morton Greene, Las Vegas, NV (US)

( * ) Notice: Subject to any disclaimer, the term of this patent is extended or adjusted under 35 U.S.C. 154(b) by 241 days.

(21) Appl. No.: 18/177,456

(22) Filed: Mar. 2, 2023

(65) Prior Publication Data

US 2023/0280300 A1     Sep. 7, 2023

Related U.S. Application Data

(60) Provisional application No. 63/315,617, filed on Mar. 2, 2022.

(51) Int. Cl.
| | |
|---|---|
| *G01N 27/327* | (2006.01) |
| *C07K 16/12* | (2006.01) |
| *C07K 16/1271* | (2026.01) |
| *C07K 16/1282* | (2026.01) |
| *C12Q 1/04* | (2006.01) |
| *G01N 21/77* | (2006.01) |
| *G01N 33/02* | (2006.01) |
| *G01N 33/543* | (2006.01) |
| *G01N 33/569* | (2006.01) |

(52) U.S. Cl.
CPC ....... *G01N 27/327* (2013.01); *C07K 16/1271* (2013.01); *C07K 16/1282* (2013.01); *G01N 33/02* (2013.01); *G01N 33/5438* (2013.01); *C12Q 1/04* (2013.01); *G01N 2021/7756* (2013.01); *G01N 33/56911* (2013.01); *G01N 2333/31* (2013.01); *G01N 2333/33* (2013.01)

(58) Field of Classification Search
None
See application file for complete search history.

(56) References Cited

U.S. PATENT DOCUMENTS

| | | | | |
|---|---|---|---|---|
| 2005/0239132 A1* | 10/2005 | Klapproth | ........ | G01N 33/54373 435/7.1 |
| 2005/0272105 A1* | 12/2005 | Levon | ...................... | C12Q 1/00 435/287.2 |
| 2016/0022185 A1* | 1/2016 | Agarwal | ............ | A61B 5/14735 427/2.12 |

FOREIGN PATENT DOCUMENTS

| | | | | |
|---|---|---|---|---|
| WO | WO-9837409 A1 * | 8/1998 | ......... | G01N 33/5438 |

* cited by examiner

*Primary Examiner* — J. Christopher Ball

(57) ABSTRACT

A bio-sensor device for the electrochemical detection of a bacterial pathogen, the device including a sample chamber and an electronic data module. The sample chamber includes passive sensing probes to detect pathogenic antigens in a sample containing the bacterial pathogen. The probes detect a reaction voltage corresponding to an antigen-antibody reaction occurring when the pathogenic antigens come into contact with an antibody specific for pathogenic antigens present in in the contents of the sample chamber and contacted by the electrical probes. The electronic data module detects and processes electrical signals detected by the conductive electrical probes corresponding to an amount of the antigen present in the sample, wherein the reaction voltage is detected at the time of the reaction.

16 Claims, 13 Drawing Sheets

No Agglutination Type A-Anti B

Visual Agglutination Type A-Anti A

Examples of Tubular Static Mixers

Sample Liquefaction

Buffer Solution used to Liquefy Sample as with Current PCR Tests

Sample Slurry for Analysis

Continuous Phage Testing with Adsorbed Phage

Electrochemical Detection Cell with Static Mixer Coated with Selective Phage

Real Time Electrochemical Monitoring and Recording Device

Metering Pump

Sample

Continuous Phage Testing for Multiple Analyates in Series

Real Time Electrochemical Monitor and Recording Device

Electrochemical Detection Cells with Static Mixer Coated with Different Selective Phages in Series Metering Pump Sample

DEVICE, PROCEDURE AND SYSTEM FOR DETECTING BACTERIAL PATHOGENS INCLUDING METHICILLIN-RESISTANT *STAPHYLOCOCCUS AUREUS* OR CLOSTRIDIUM DIFFICILE

CROSS-REFERENCE TO RELATED APPLICATION

This application claims the benefit of U.S. Provisional Application Ser. No. 63/315,617, filed by Clifford H. Kern III et al. on Mar. 2, 2022, and, is a Continuation-in-Part of U.S. application Ser. No. 16/246,172, filed by Clifford H. Kern III, et al. on Jan. 11, 2019, which claims the benefit of U.S. Provisional Application Ser. No. 62/709,278, filed by Clifford H. Kern III, et al. on Jan. 12, 2018, entitled, "TESTING DEVICE, PROCEDURE AND SYSTEM FOR METHICILLIN-RESISTANT *STAPHYLOCOCCUS AUREUS* AND *CLOSTRIDIUM DIFFICILE,*" commonly assigned with the applications and incorporated herein by reference.

TECHNICAL FIELD

This application is directed, in general, to a biosensor device and, more specifically, to a bio-sensor device for the electro-chemical detection of certain bacterial pathogens.

BACKGROUND

The rapid detection of bacterial pathogens, such as *Staphylococcus aureus* and *Clostridium difficile*, is important to the early diagnosis and treatment of patients, mitigating the spread of such pathogens and confirming that surfaces potentially contaminated with such pathogens have been de-contaminated.

SUMMARY

One aspect provides a bio-sensor device for the electro-chemical detection of a bacterial pathogen. The device includes a sample chamber and an electronic data module. The sample chamber includes electrical probes to detect the reaction of a specific test antibody with a corresponding pathogenic antigen in a sample containing that bacterial pathogen. The electrical probes detect a reaction voltage created by the an antigen-antibody reaction which occurs when the pathogenic antigens come into contact with an antibody specific for pathogenic antigens present in an appropriate medium in the sample chamber in contact with the signal detecting probes. The electronic data module detects and processes electrical signals from the signal detecting probes corresponding to an amount of the antigen present in the sample, wherein the reaction voltage is detected at the time of the reaction.

In some such embodiments, the bacterial pathogen is one of methicillin-Resistant *Staphylococcus aureus, Clostridium difficile* or a combination of methicillin-Resistant *Staphylococcus aureus* and *Clostridium difficile*. In some such embodiments, the pathogen is detected from direct testing of a swab, or washings from a surface. In any such embodiments, the surface can be an epidermis of an organism, a potentially contaminated non-biologic surface including a counter-top, synthetic athletic playing surface, wound dressing, or equipment.

In any such embodiments, the device can be configured as a real-time detection device for detecting the presence of the pathogenic antigens, and the real-time detection device can be self-contained and field-applicable, not requiring external equipment or highly trained laboratory personnel. In some such embodiments, the signal detecting probes of the real-time detection device can be configured to respond to electrochemical antigen-antibody events corresponding to the antigen-antibody reaction within 60 seconds of the sample containing the pathogenic antigens and the antibody-containing reaction medium in the sample chamber becoming in contact with each other. In some such embodiments, the real-time detection device can be configured for direct electrochemical reaction detection of the antigen-antibody reaction. In some such embodiments, such real-time detection device is not sensitive to detection of reaction products of the antigen-antibody reaction, but only to the energy change created by the interaction of the reactants.

In any such embodiments, the antibody specific for the pathogenic antigens can be coated onto one or more of the sensing electrodes. In any such embodiments, the antibody specific for the pathogenic antigens can be coated or adsorbed onto a passive filler located within the sample chamber. In any such embodiments, the sample chamber includes a port for introducing a liquid reagent containing the antibody specific for the pathogenic antigens.

BRIEF DESCRIPTION

Reference is now made to the following descriptions taken in conjunction with the accompanying drawings, in which.

DETAILED DESCRIPTION

A device and methods are described for the real time direct electrochemical detection of Methicillin-Resistant *Staphylococcus aureus* (MRSA) and *Clostridium difficile* (C. Diff.) where pathogens are detected as a result of an antigen-antibody reaction. The reaction itself is detected without need for gene or molecular amplification, isolation, separation, or labeling of the products of the reaction. Such devices and methods, involving particular antigen-antibody reactions, are useful in detection of pathogens and contaminants found in infectious disease and in food and water safety applications. The real time speed, specificity, simplicity and broad applicability of the devices and methods described represent improvements to the current art.

We report here, use of a 2 minute direct Antigen-Antibody reaction based test to enable a selective real time screening system (Greene and Yokley, US Application 20100330662 At, Apparatus, System and Method for Consumer Detection of Contaminants in Foodstuffs. Dec. 30, 2010, and subsequent filings, incorporated by reference herein in its entirety).

A selective sensor has been demonstrated based on electrochemical detection of a specific antigen-antibody reaction. This electrochemical method has been previously described as a method of tracking for a wide variety of chemical reactions (W. Tison Wyatt, U.S. Pat. No. 5,749, 986, Control of Batching and Curing Processes. May 12, 1998, incorporated by reference herein in its entirety).

The selectivity required in the sensing is determined by detecting a specific fast antibody-antigen reaction. Thus, slow and complex separation, incubation and amplification steps are avoided. This selectivity and specificity are particularly useful in real-time rapid field and consumer level field detection units.

A wide variety of sample configurations can be used on this platform, from probes to flow types. Likewise, sample types including, but not limited to saliva, water, washings, homogenates, blood, or other biologic fluids can be tested.

Figure 1:
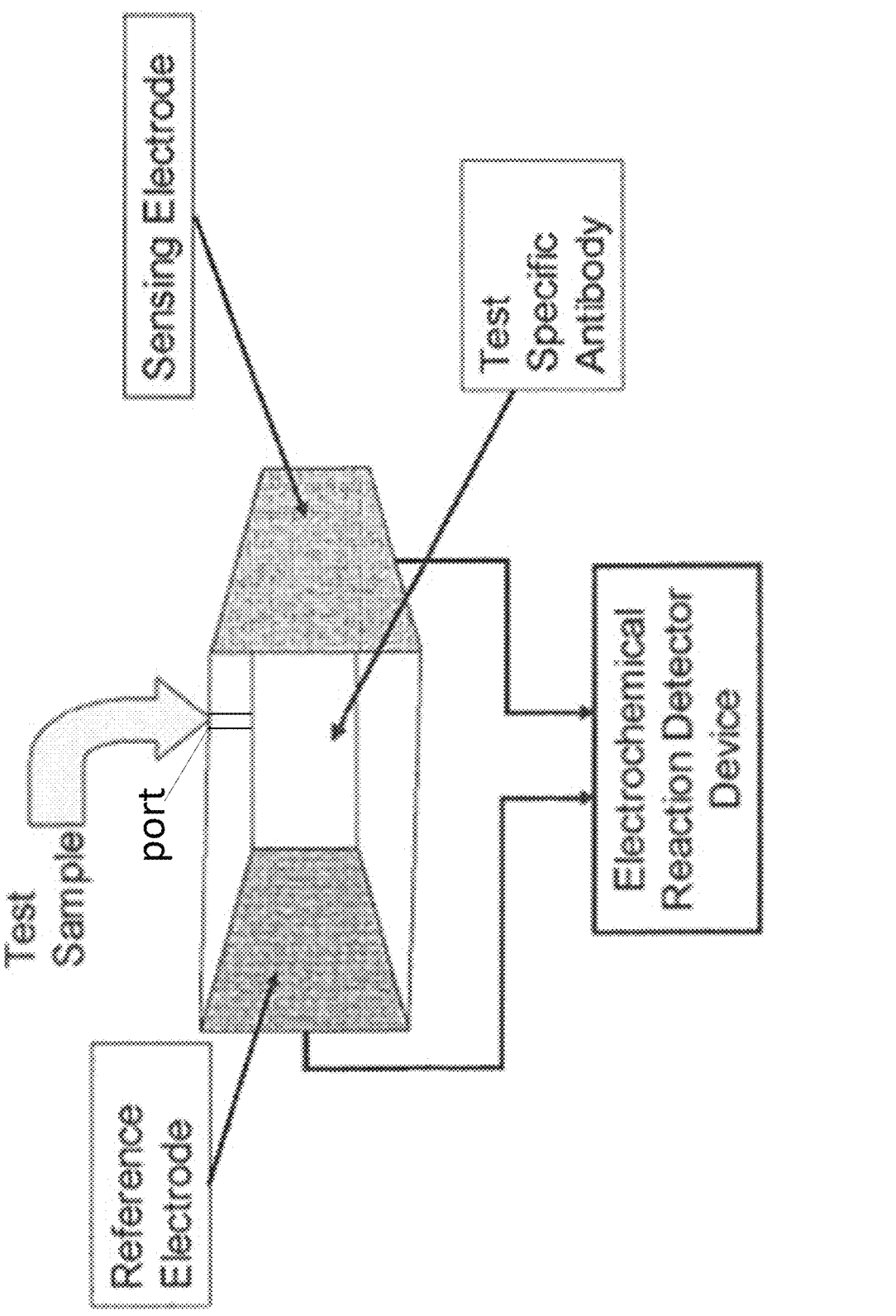
FIG. 1 shows an embodiment of the bio-sensor device.

In one embodiment (FIG. 1), the antigen test biosample and the test antibody are added to an appropriately configured electrochemical cell (e.g., via port). This configuration is useful in dealing with infectious outbreak situations. The test chamber and detector device can be contained in the same or different device modules to reduce pathogen handling risk and cost.

Figure 2:
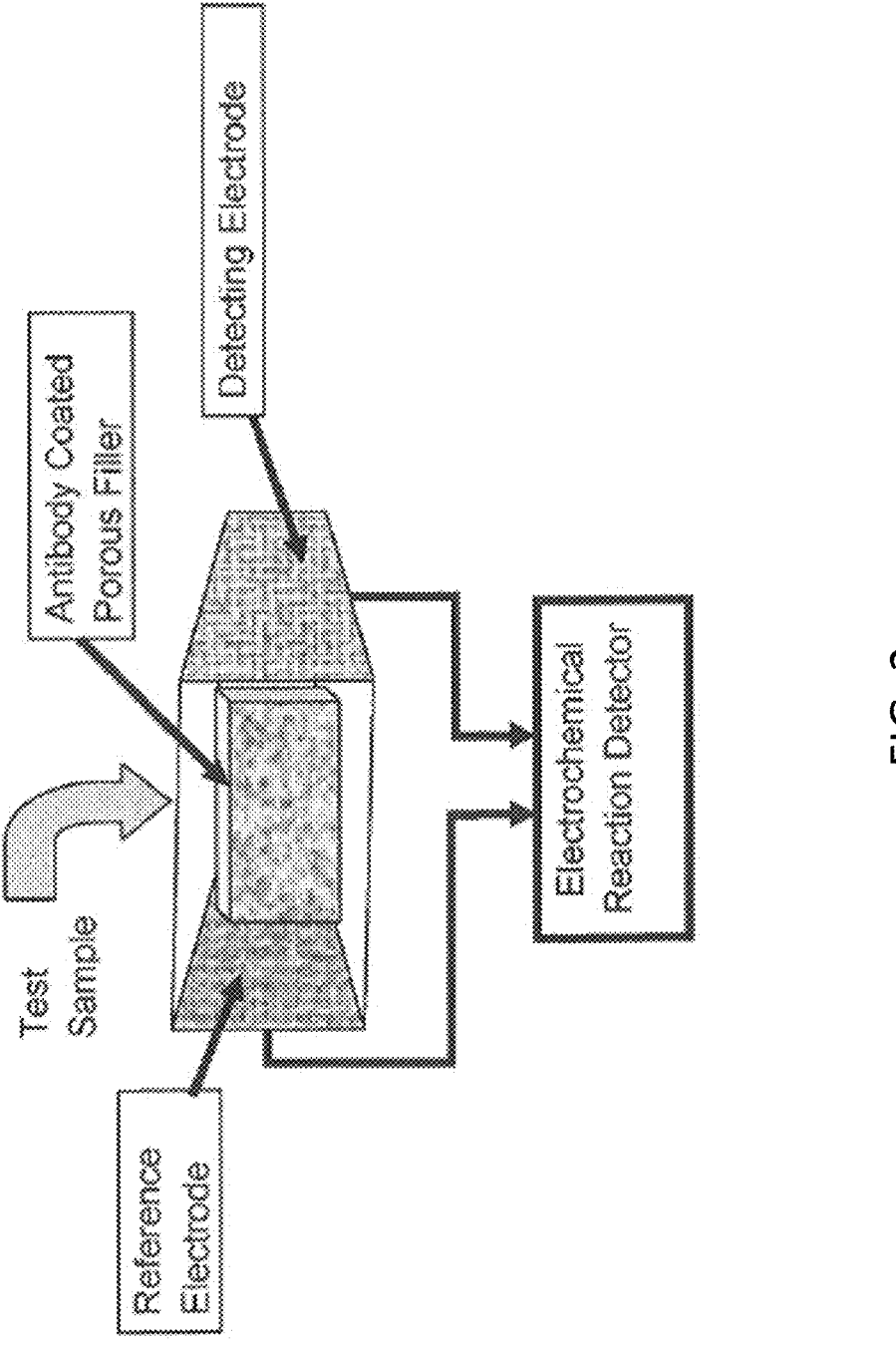
FIG. 2 shows another embodiment of the bio-sensor device.

In another embodiment (FIG. 2), the antibody is coated onto a porous or fibrous insulating material that is positioned between the electrodes. The sample is then placed in contact with the assembly and the presence or absence of an antigen-antibody reaction is determined by reaction voltage. This configuration is suitable for both small and large sample containers.

In another embodiment, the coated electrode or coated interstitial filler is positioned at the end of a probe or stick, which is connected to a detector directly or by wiring. In this embodiment, the detector is dipped or delivered into the sample. The presence of the specific antigen-antibody reaction is then detected in a similar manner as previously described.

Figure 3:
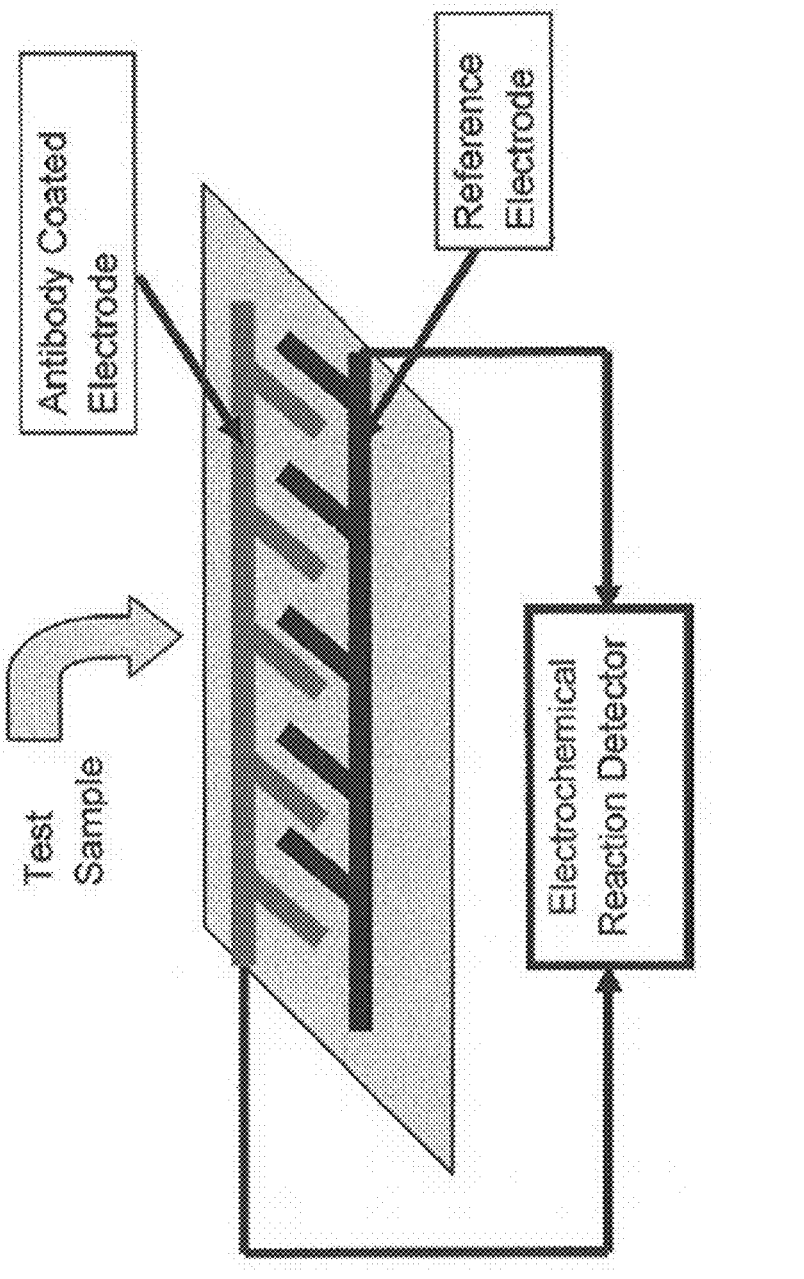
FIG. 3 shows an embodiment of the electrode probes.

In another favorable embodiment (FIG. 3), the electrodes are laid out in a planar parallel or interdigitated configuration, as shown below. In this embodiment, the reacting antibodies may be present in a solution above the planar array, coated on one electrode, or present in a porous or fibrous carrier located above the array.

Electrodes can be made of electrically similar conductive materials such as stainless steel, carbon, aluminum, nickel or copper. Non-conductive material can be plated with a layer of electrically conductive matter. The form factor can be plates, wire, wire bundles, foams or other suitable types.

In some embodiments coating one electrode or intracellular filler with a specific antibody, it then is possible to determine the presence of that specific corresponding antigen within the test sample. The selectivity required in the sensing is determined by the antibody-antigen reaction. In this way, slow and complex separation, incubation and amplification steps are avoided. This selectivity is particularly useful in rapid field and consumer level field detection units.

Further, several test chambers can be placed in series so that the sample flows from one test chamber to another, where each test chamber contains an antibody, either coated or free, specific to a different biological material or pathogen of interest. In this way, for example, a single vegetable homogenate sample could be tested for the presence of multiple pathogens such as Salmonella and E. coli which are concerns in food safety applications, in a single test pass.

The configurations described permit real time detection of specific antigens with high sensitivity. The ultimate sensitivity of the method is determined by the antigen and antibody concentrations as well as the specificity of the antibody against the pathogen or contaminant. The reaction is rapid, without the need for long sample incubation or the use of additional reagents.

It is also possible to provide mixtures of antibodies in the chamber or probe. This arrangement would allow for the detection of multiple strains of the same pathogen, or for mixtures of antigens that might be characteristic of a condition of interest. (See for example the recent report linking pancreatic cancer risk with a characteristic group of oral bacteria. http:1/news.brown.edu/pressreleases/2012/09/periodontic. Dominique S Michaud, Jacques Izard, CharlotteS Wilhelm-Benartzi, Doo-Ho You, Verena A Grote. Anne Tjczmneland. Christina C Dahm, Kim Overvad. Mazda Jenab, Veronika Fedirko, Marie Christine Boutron-Ruault, Frangoise Clavei-Chapelon, Antoine Racine, Rudolf Kaaks, Heiner Boeing, Jana Foerster. Antonia Trichopoulou, Pagona Lagiou. Dimitrios Trichopoulos, Carlotta Sacerdote. Sabina Sieri, Domenico Palli, Rosario Tumino, Salvatore Panico, Peter D Siersema. Petra H M Peeters, Eiliv Lund, Aurelio Barricarte, Jose-Maria Huerta, Esther Molina-Montes, Miren Dorronsoro, J Ramon Quiros, Eric J Duell, Weimin Ye, Malin Sund, Bjorn Lindkvist, Dorthe Johansen, Kay-Tee Khaw, Nick Wareham, Ruth C Travis, Paolo Vineis, H Bas Bueno-de-Mesquita, Elio Riboli. Plasma antibodies to oral bacteria and risk of pancreatic cancer in a large European prospective cohort study. Gut, 18 Sep. 2012 DOI: 10.1136/gutjnl-2012-303006)

Reaction chambers made of various materials and in a variety of sizes most preferably glass, silicon or a polymeric material. For quick field tests for contamination of food or drinking water samples, a small test chamber of 1-10 ml might be most appropriate. When testing samples of meat or vegetables for contamination, larger sample containers, designed to hold between 10 to 100 ml of a liquefied preparation may be better suited.

In a preferred embodiment, the reaction chamber is molded in two halves which can be snapped together to form a reaction chamber. In this embodiment, the antibody coated electrode is produced and packaged separately in one half chamber. The reference electrode is assembled and attached to the other half. Manufacturing is therefore simplified. It is then possible to mix and match sensors for various antigens from the smallest number of parts.

This described invention can be at a modular breadboard stage of development. Several integrated product configurations of the probes/chambers and the intermediate electronics and the computer/tablet/smartphone data logging device, as required by the specific application are possible. The form factor can be plates, wire, wire bundles, foams or other suitable types. These might include hand held, and devices where the test chamber unit contains a wireless communication module so that the chamber is never touched by anyone other than the subject providing the sample.

Signal detecting electrodes can be made of any of several electrically similar conductive materials such as stainless steel, carbon, aluminum, nickel or copper, gold or silver, tungsten, and any of their conductive compounds or alloys.

Several examples are described below:

Example One

Real Time Detection of Blood Typing Antigen-Antibody Reaction with Visual Confirmation via Agglutination ABO Blood type is determined by antigens on the surface of red blood cells. When exposed to a specific antibody, the blood cells will agglutinate. For example, a drop of Type A blood mixed with Anti-A antibody will develop a granular appearance on a glass slide as the cells agglutinate. A drop of Type B blood mixed with the same antibody will remain homogeneous in appearance.

Using Carolina Biological Supply Blood Typing Kit #700122, which uses simulants, we conducted an experiment in which we mixed Type A blood with Type A Antibody, Type A blood with Type B antibody, Type B blood with Type B Antibody, and Type B blood with Type A Antibody. As expected, we observed agglutination only with Type B Anti B and Type A-Anti A.

Figure 4:
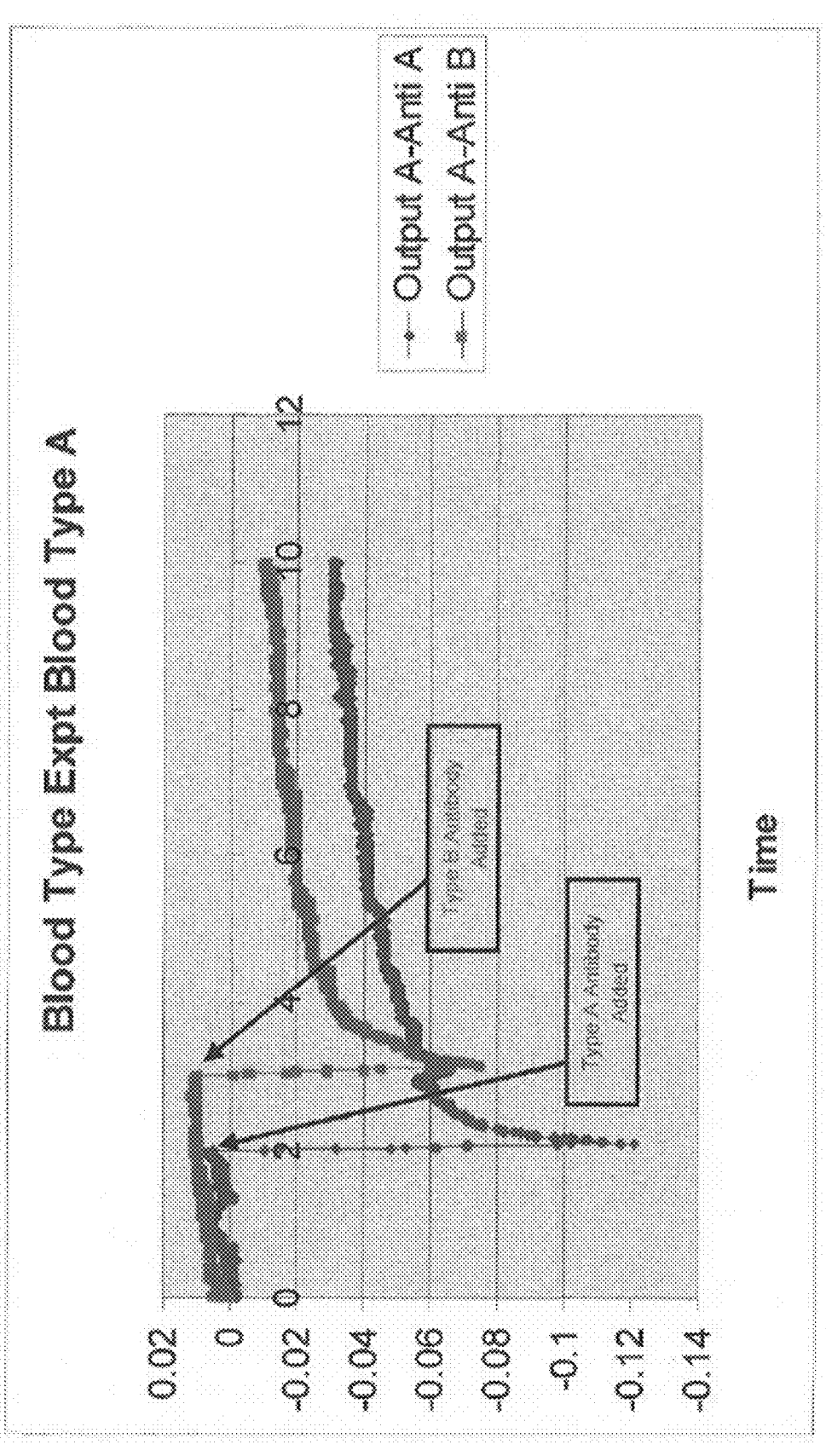
FIG. 4 shows a plot of time versus Output Anti-A and Anti-B for Blood Type Expt Blood Type A.
Figure 5B:
FIGS. 5A and 5B show images of visual Agglutination type Anti-A (FIG. 5A) and Anti-B (FIG. 5B)
Figure 5A:
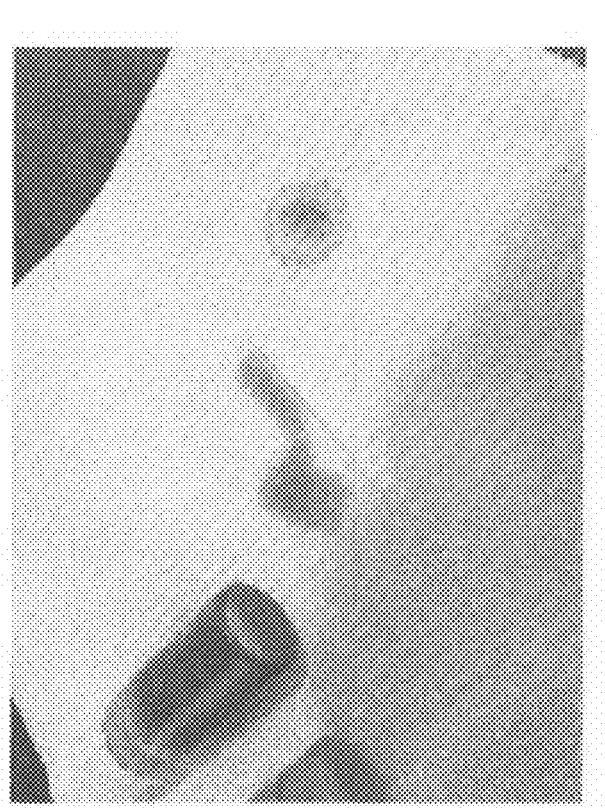

Once the activity of the samples was confirmed, we did the same experiment using the technology presented in this proposal. The results are illustrated in the charts and photographs shown below (FIGS. 4-5B), indicating expected reactions visually and by change in electrical potential.

Example Two

Selective Real Time Sensor Detection: Antigen-Antibody Solution Reaction

Three Goat Anti-albumin samples for equine, bovine, and porcine albumin were prepared in distilled water in individual vials. Each sample vial was equipped with an ElectroImmune sensor probe. Each sample, in turn was connected to the ElectroImmune sensor. Bovine Albumin supplied in the same kit was added to the chamber.

Figure 6:
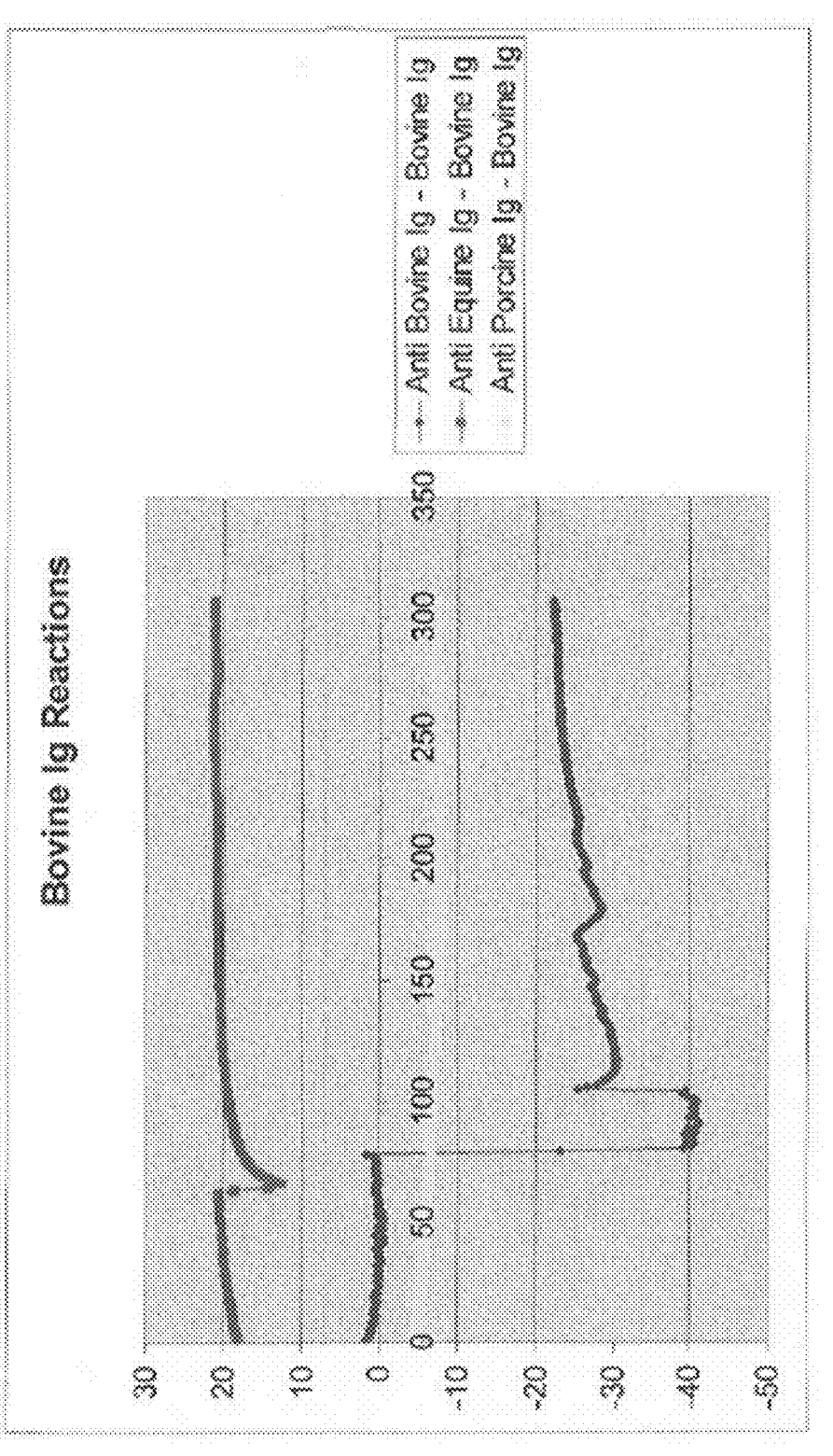
FIG. 6 shows Bovine Ig Reactions.

The results of the experiment are summarized in Table 1, and the sensor output traces are shown below (FIG. 6).

TABLE 1

Antigen-Antibody Detection via Sensor Reaction

| Antibody | Antigen | Result |
|---|---|---|
| Goat Anti-Bovine Albumin | Bovine 1 g Albumin | Immediate Reaction on Mixing |
| Goat Anti-Equine Albumin | Bovine 1 g Albumin | No Reaction |
| Goat Anti-Porcine Albumin | Bovine 1 g Albumin | No Reaction |

Thus, specificity of the method is demonstrated.

Example Three

A bacterial detection demonstration was conducted as follows. A suspension of polyclonal *Escherichia coli* antibody [Pierce Antibodies, #PA125636] in saline was challenged with a commercial *E. coli* [Carolina Biologicals, #124300] solution in an electrochemical test chamber. The electrochemical reaction trace was recorded on a PC level platform.

Figure 7:
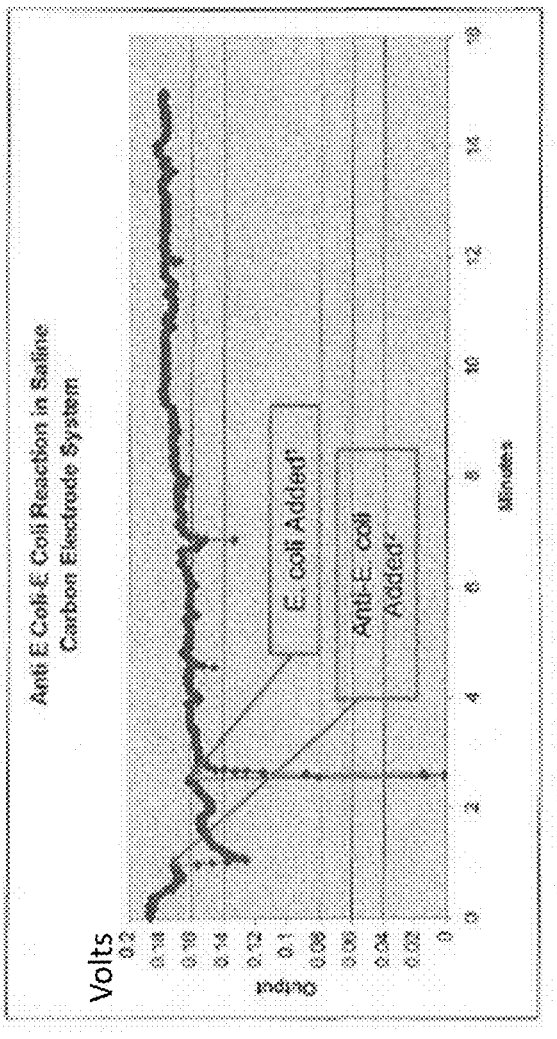
FIG. 7 shows a plot of time versus output of Real Time Detection of Anti *E. coli-E. coli* Reaction.

The antigen-antibody reaction produced a real time electrochemical displacement signal which was readily detected and repeatable (FIG. 7).

Embodiment can be a breadboard level device which will detect antigen-antibody reactions in real time by electrochemical detection, suitable for detection of a bacterial infection pathogen ex vivo. This configuration is based on our previous antigen-antibody demonstration work. Further, as described above, numerous configurations to expose the sample material to the appropriate antibody of interest are possible and will depend on the specific needs for the test involved. Hospital and wound derived infections such as Methicillin-resistant *Staphylococcus aureus* [MRSA] and *Clostridium difficile* (*C. difficile*), a bacterium that causes diarrhea and more serious intestinal conditions such as colitis, are a particular concern.

Strains that are oxacillin and methicillin resistant, historically termed methicillin-resistant *S. aureus* (MRSA), are resistant to all B-lactam agents, including cephalosporins and carbapenems, although they may be susceptible to the newest class of MRSA-active cephalosporins (e.g, ceftaroline). Strains of MRSA causing healthcare-associated infections often are multiply resistant to other commonly used antimicrobial agents, including erythromycin, clindamycin, fluoroquinolones and tetracycline, while strains causing community-associated infections are often resistant only to B-lactam agents and erythromycin, may be resistant to fluoroquinolones. Since 1996, MRSA strains with decreased susceptibility to vancomycin (minimum inhibitory concentration [MIC], 4-8 j . . . 1 g/ml) and strains fully resistant to vancomycin (MIC 32 j . . . 1 g/ml) have been reported (https://www.cdc.gov/mrsa/lab/index.html)

Table 2 presents a summary of types of clinical of MRSA tests, shown here for reference (E. Sturenburg, GMS German Medical Science 2009, Vol. 7, ISSN 1612-3174.).

TABLE 2

| Test | Distributor | Test concept | Turn-around time | Costs/ swab | System can be used with swabs from | Author year [Ref] | Performance data |
|---|---|---|---|---|---|---|---|
| I Single-locus PCR: SCCmec PCR; suitable for point-of-care testing | | | | | | | |
| GeneXpert MRSA | Genzyme Virotech | GeneXpert DX Cycler; single-use cartridges containing freeze-dried beads with all reagents required for PCR | 75 min | 25-35 € | nose | Cepheid 2007 [38]; Rossney 2008 [39] | Sens: 86.3% Spec: 94.9% PPV: 80.5% NPV: 96.6% Sens: 90% Spec: 97% PPV: 86% NPV: 98% |

TABLE 2-continued

| Test | Distributor | Test concept | Turn-around time | Costs/swab | System can be used with swabs from | Author year [Ref] | Performance data |
|---|---|---|---|---|---|---|---|
| II Single-locus PCR: SCCmec-PCR | | | | | | | |
| BD GeneOhm MRSA | Becton Dickinson | SmartCycler | <2 h | 20 € | nose | Huletsky 2004 [28]; Desjardins 2006 [34]; de San 2007 [33]; Boyce 2008 [32]; Oberdorfer 2008 [31] | Sens: 98.7% Spec: 95.4% PPV: na NPV: na Sens: 96% Spec: 96% PPV: 90% NPV: 98% Sens: 96% Spec: 96% PPV: 90% NPV: 98% Sens: 100% Spec: 98.6% PPV: 95.8% NPV: 100% Sens: 100% Spec: 98.6% PPV: 95.8% NPV: 100% |
| GenoType MRSA Direct | Hain Lifesciences | Conventional cycling followed by line-blot assay | 4-5 h | 14 € | nose, throat, hairline, wounds | Holfelder 2006 [30] | Sens: 93-95% Spec: 99% PPV: 85-88% NPV: 99% |
| III Multilocus PCR: mecA plus *S. aureus* marker gene plus CoNS marker genes | | | | | | | |
| hyplex Staphylo Resist | BAG | (mecA + *S. aureus/S. epidermidis/S. haemolyticus*-specific sequence)/ conventional cycling followed by enzym-immuno assay | 4-5 h | 10 € | swabs (not specified), respiratory aspirates | Leven 2007 [27]; Koelemann 2005 [26] | Sens: 93% Spec: 96% PPV: 83% NPV: 98% Sens: 100% Spec: 95% PPV: 61% NPV: 100% |
| LightCycler *Staphylococcus/* MRSA Kit | Roche Diagnostics | (mecA + 16S-23S ITS sequence (with melting point analysis of the species)/ LightCycler | <2 h | 15-20 € | swabs (not specified) | Kola 2005 [25] | Sens: 89% Spec: 97% PPV: 60% NPV: 99.4% |
| IV Rapid culture/without any nucleic acid amplification | | | | | | | |
| 3M BacLite Rapid MRSA Test | 3M Company | Selective broth enrichment > magnetic microparticle separation > lysostaphin lysis > bioluminescence measurement | 5 h | 10 € (96 samples/ day) | nose, groin | O'Hara 2007 [18]; Cohen 2007 [19] | Sens: 94.6% Spec: 96.9% PPV: na NPV: na Sens: 95.9% Spec: 88.8% PPV: na NPV: na |

Abbreviations/annotations
GeneXpert DX system, fully automated platform for real-time PCR cycling, only little operator handling/knowledge required, works with single-use disposable cartridges containing all PCR reagents required; 16S-23S ITS, 16S-23S rDNA internal transcribed spacer region; CoNS, Coagulase-negative *staphylococci*: LightCycler, special instrument for real-time PCR cycling; mecA, gene conferring methicillin resistance in *staphylococci*; SmartCycler, special instrument for real-time PCR cycling, only little operator handling/knowledge required; SCCmec-orfX, DNA sequence in the region of the open reading frame orfX, where the staphylococcal cassette chromosome mec (SCCmec) integrates into the *S. aureus* chromosome. SCCmec carries the resistance determinant mecA.
NPV, negative predictive value; Sens, sensitivity; Spec, specificity; PPV, positive predictive value; na, not available.

*Clostridium difficile* (*C. difficile*) is a bacterium that is related to the bacteria that cause tetanus and botulism. The *C. difficile* bacterium has two forms, an active, infectious form that cannot survive in the environment for prolonged periods, and an inactive, "noninfectious" form, called a spore, that can survive in the environment for prolonged periods. Although spores cannot cause infection directly, when they are ingested they transform into the active, infectious form.

*C. difficile* spores are found frequently in: hospitals, nursing homes, extended care facilities, and nurseries for newborn infants.

They can be found on: bedpans, furniture, toilet seats, linens, telephones, stethoscopes, fingernails, rings, jewelry), floors, infants' rooms, and diaper pails.

They even can be carried by pets. Thus, these environments are a ready source for infection with *C. difficile* (https://www.medicinenet.com/*Clostridium difficile* colitis/article.htm).

Antibiotic-associated (*C. difficile*) colitis is an infection of the colon caused by *C. difficile* that occurs primarily among individuals who have been using antibiotics. *C. difficile* infections are commonly acquired during hospital stays, infecting approximately 1% of patients admitted to hospitals in the United States. *C. difficile* may also be acquired in the community, however.

It is the most common infection acquired by patients while they are in the hospital. More than half a million *C. difficile* infections occur in hospitals in the US each year, with about 300,000 occurring while in the hospital or shortly after hospitalization. After a stay of only two days in a hospital, 10% of patients will develop infection with *C. difficile*. *C. difficile* also may be acquired outside of hospitals in the community. It is estimated that about 200,000 infections with *C. difficile* occur in the community unrelated to hospitalization each year in the U.S.

Diagnosis of *Clostridium difficile* infection is based on clinical presentation and laboratory tests. Although numerous laboratory methods are now available, the diagnosis of *C. difficile* infection remains challenging. Nucleic acid amplification tests (NAATs) are the most recent marketed methods. These methods detect genes for toxins A and/or B. They are very sensitive compared with the reference method (toxigenic culture). However, these test require specialized equipment and are not rapid enough for use in the field or in a physician's office.

Further described below are embodiments of a method and devices for the real time direct detection of pathogens and contaminants in food by means of detecting the reaction with selective bacteriophages, in particular use of a 2 minute direct Bacteriophage-Bacteria reaction based test to enable a selective real time screening system.

A selective sensor has been demonstrated based on electrochemical detection. This electrochemical method has been previously described as a method of tracking a wide variety of chemical reactions.

The selectivity required in the present novel invention is determined by detecting a specific fast bacteriophage-bacteria interaction. Thus, commonly used slow and complex sample separation, incubation and amplification steps are avoided. This selectivity and specificity are particularly useful in real time rapid field and consumer level field detection units.

Signal-detecting electrodes in the sensor can be made of any of several electrically similar conductive materials including, but not limited to stainless steel, carbon, aluminum, nickel or copper. The form factor can be plates, wire, wire bundles, foams or other suitable types.

In some embodiments coating one electrode or intracellular filler with a specific bacteriophage, it is possible to determine the presence of that specific corresponding pathogen within the test sample. The selectivity required in the sensing is determined by the bacteriophage-bacteria reaction. Further, several test chambers can be placed in series so that the sample flows from one test chamber to another, where each test chamber contains electrodes with a specific bacteriophage, either coated or free, specific to a different bacterial strain or pathogen of interest. In this way, for example, a single food homogenate sample could be tested for the presence of both *Salmonella* and *Escherichia coli* variants in a single test pass.

The configurations described permit real time detection of specific bacteria with high sensitivity. The ultimate sensitivity of the method is determined by the bacteriophage and bacteria concentrations. The reaction is rapid, without the need for long sample incubation or the use of additional reagents.

It is also possible to provide mixtures of bacteriophage strains in the chamber or probe. This arrangement would allow for the detection of multiple strains of the same pathogen, or for mixtures of pathogens that might be characteristic of a condition of interest.3

Reaction chambers can be made of various materials and in a variety of sizes most preferably glass, silicone, a polymeric, or other inert, non conductive material. For quick field tests for contamination of food or drinking water samples, a small test chamber, for example, of 1-10 ml might be most appropriate. When testing samples of meat or vegetables for contamination, larger sample containers, designed to hold between 10 to 100 ml of a liquefied preparation to be tested in a static or flow chamber may be better suited.

The detection described here, is of the reaction resulting from the interaction of the bacteriophage and the corresponding bacteria. No energy or stimulation from an external source is employed.

In one embodiment, the reaction chamber is molded in two halves which can be snapped together to form a reaction chamber. In this embodiment, the selective bacteriophage coated electrode is produced and packaged separately in one half chamber. The reference electrode is assembled and attached to the other half. Manufacturing is therefore simplified. It is then possible to mix and match sensors for various antigens from the smallest number of parts.

In another embodiment, the reaction chamber consists of a tubular reactor from approximately 1 inch to approximately 12 inches in length and 0.25 inches to 2 inches in diameter. This tubular reactor is uniquely fitted with a static mixing device to form a high contact continuous reaction chamber. The resulting chamber is then fitted with high sensitivity electrodes, to produce a continuous passive electrochemical test cell. The interaction of the bacteriophage with the pathogen bacteria produces an electrochemical event that is detected by passive electrodes at the inner surface of the test cell. This configuration is particularly efficacious in food pathogen testing, where 200 to 400 gram samples are tested for extremely low levels of pathogen content.

Figure 8:
FIG. 8 shows example embodiment static mixers.

The sample analyate solution is then pushed through the tubular reactor at a rate to provide sufficient time in the reaction zone for the rapid bacteriophage-bacteria reaction to take place (FIG. 8, Example static mixers)

Figure 9A:
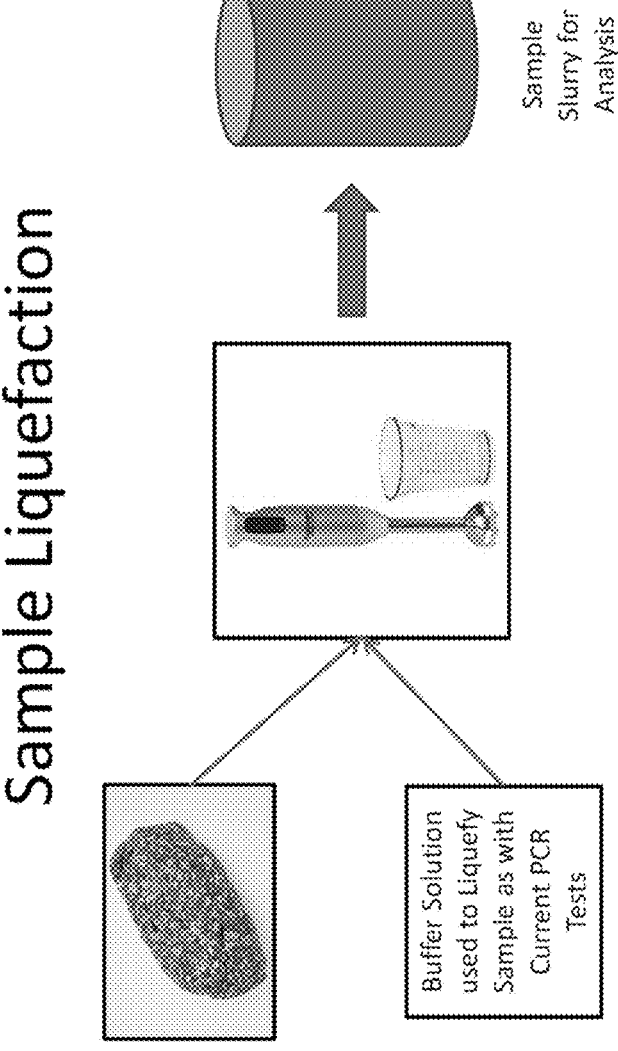
FIG. 9A shows example sample liquefaction.
Figure 9B:
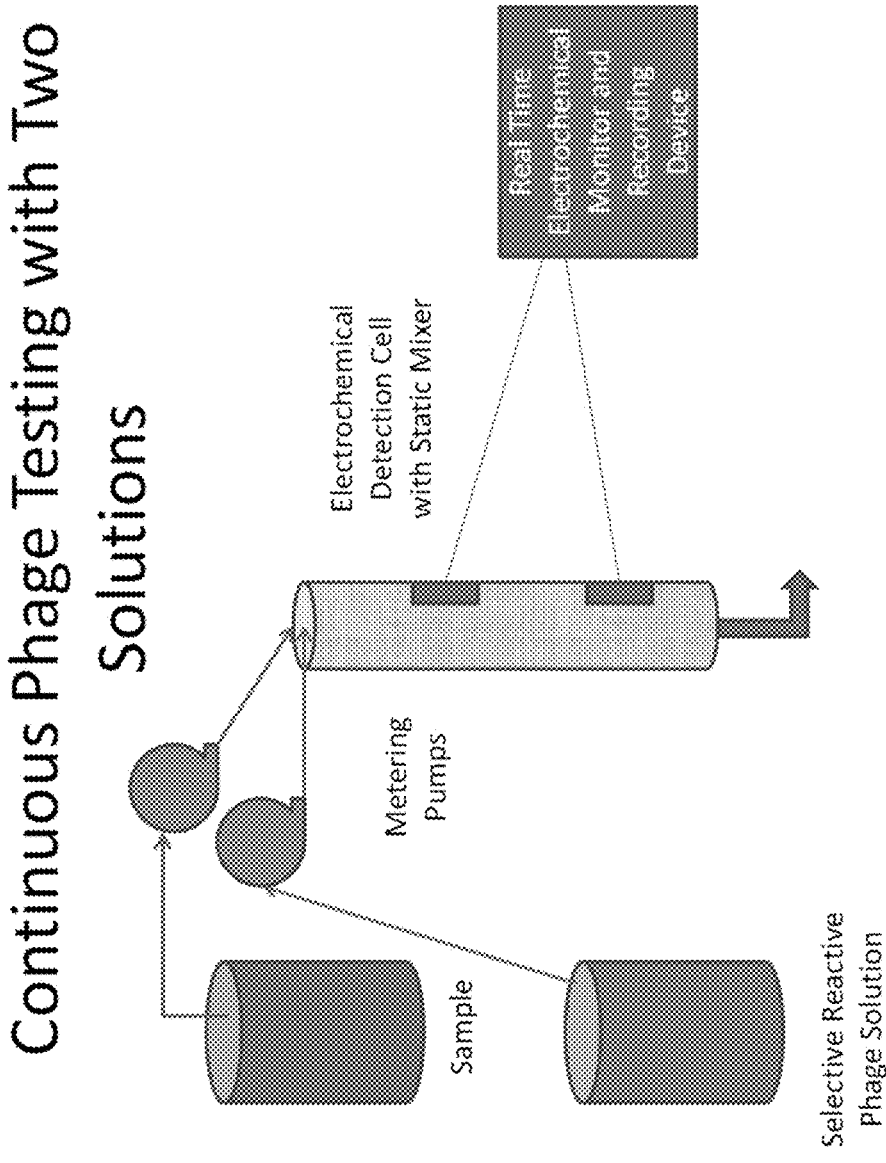
FIG. 9B shows example continuous phage testing with two solutions.

In these cases, the sample to be tested, whether meat, leafy greens, dairy or other products are liquefied by means of procedures known in the art to prepare samples for contamination testing or PCR amplification. The liquefied sample is then pushed through the continuous detection cell either to be mixed with a solution of pathogen-specific bacteriophage, for real time reaction based detection (FIG. 9A Example Sample Liquefaction, 9B Example Continuous Phage Testing with two solutions)

Figure 10A:
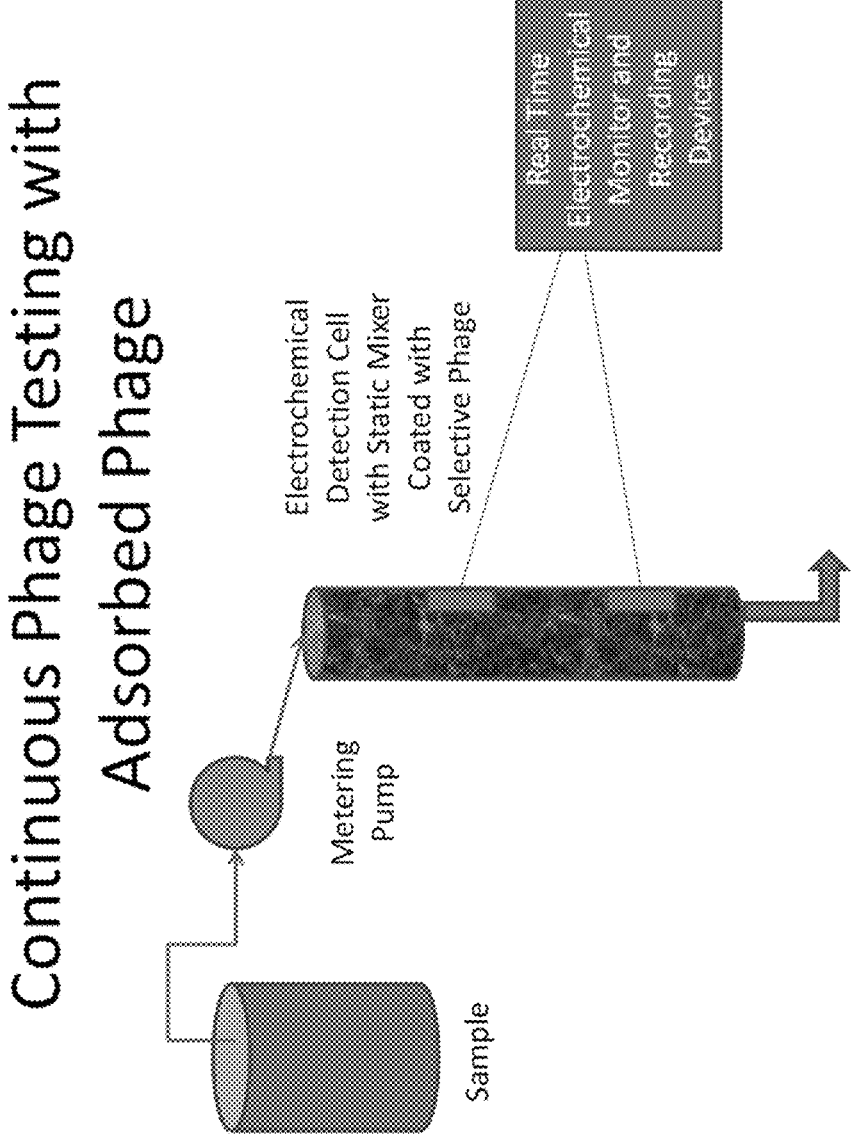
FIG. 10A shows example continuous phage testing with absorbed phage.
Figure 10B:
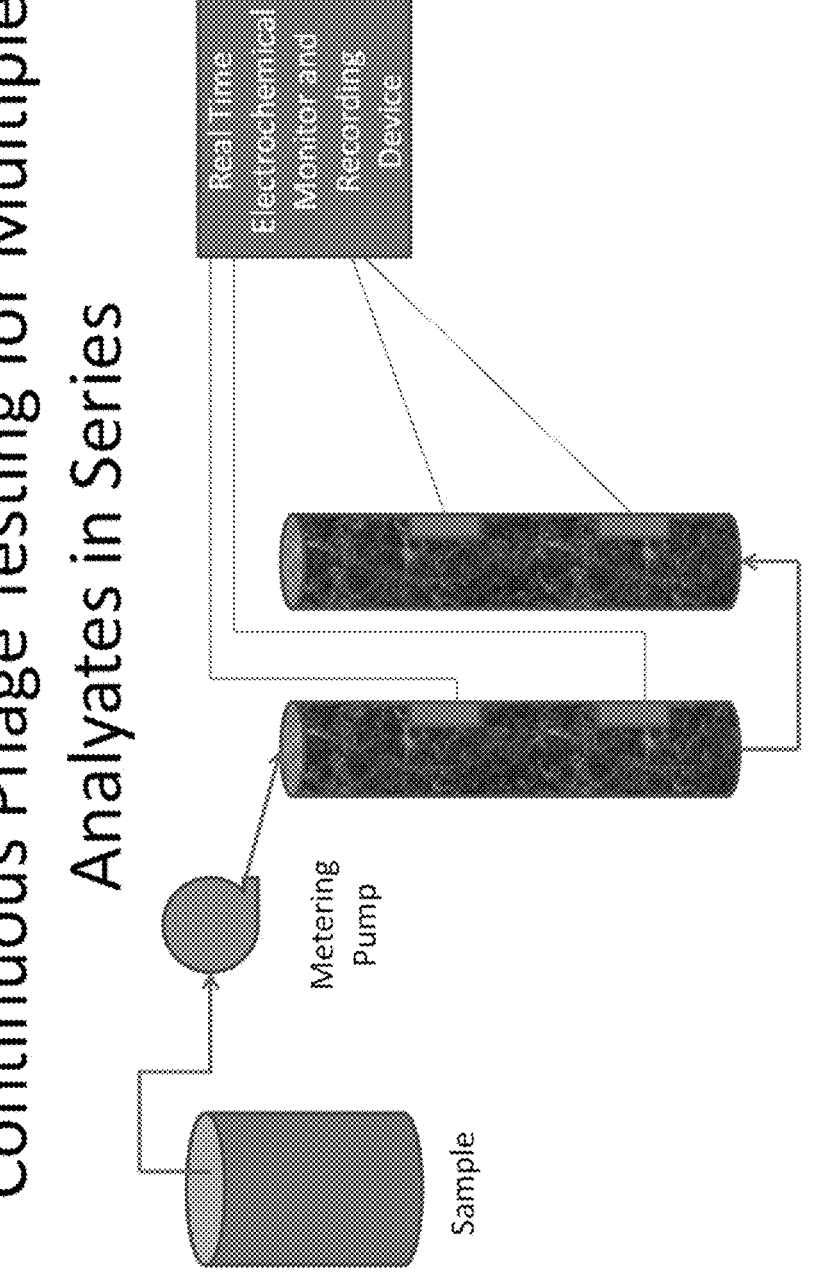
FIG. 10B shows example continuous phage testing for multiple analyates in aeries.

In another embodiment, the selective bacteriophage can be adsorbed onto the surface of the static mixer within the test chamber, and only the test sample solution is then required. This configuration offers the opportunity to test the same sample for the presence of multiple pathogens of interest in series on a real time basis. This test configuration is illustrated in the diagram below. (FIG. 10A Example Continuous Phage Testing with Absorbed Phage; 10B Example Continuous Phage Testing for Multiple Analyates in Series)

Embodiments of the device invention can be at a modular breadboard stage of development. Several integrated product configurations of the probes/chambers and the intermediate electronics and a computer/tablet/smartphone data logging device, as required by the specific application are possible.

Signal-detecting electrodes can be made of any of several electrically similar conductive materials such as stainless steel, carbon, aluminum, nickel or copper, gold or silver, tungsten, and any of their conductive compounds or alloys. The form factor can be plates, wire, wire bundles, foams or other suitable types. These can include hand devices, and devices where the test chamber unit contains a wireless communication module so that the chamber is never touched by anyone other than the subject providing the sample.

Further example testing is described below:

In our work to determine the limit sensitivity of the passive electrochemical sensors to detect specific biochemical reactions, we utilized commercial Bacteriophage T4 that was available in standardized concentration [Carolina Biological Supply, Item #1234545]. We investigated the rapid real time infection event of serially diluted Bacteriophage T4 samples of concentrations infecting excess available *Escherichia coli*. The infection reaction events produced an electrochemical trace that was easily recorded using the passive detection device of this invention.

Results are shown in the Table below.

To determine the sensitivity of the method, we investigated the potential electrochemical detection of the infection of *E. coli* bacteria by Bacteriophage T4. This is a complex infection process, and represents an extension of our application base. At the same time this reaction provides an opportunity to investigate the virus concentration sensitivity of our methods, since Coliphage T4 could be purchased in solution with known standardized lot titer.

In this example, serial dilutions of commercial Coliphage T4 in Peptone solution were placed in an electrochemical detection cell with a small standard quantity of Peptone to insure electrode coverage. Aliquots of *E. coli* were added to the cell to be in excess relative to the T4 test material. Immediate electrochemical responses were observed on addition of the bacteria. In general the amplitude of the response declined with the decreasing concentration of the Coliphage, however since this is a detection method, rather than a quantitative assay, no attempt was made to establish concentration correlations at this time.

Figure 11:
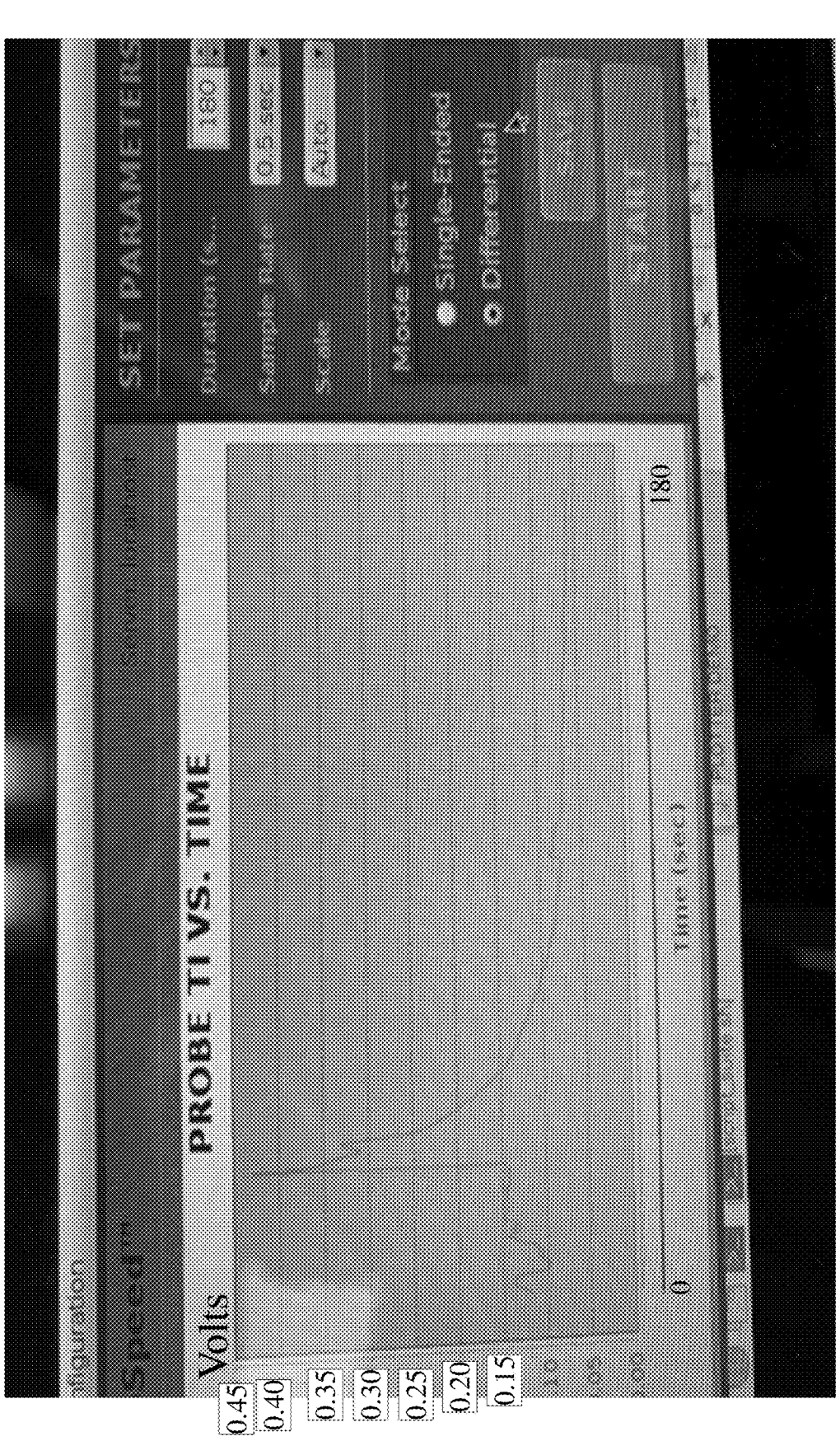
FIG. 11 shows an example response curve.

An example response curve of output (presented as a reaction voltage corresponding to electrochemical energy produced by the antigen-antibody reaction) versus time is shown in FIG. 11. The duration of the experiment trace was three minutes (180 s).

Experimental

Coliphage T4r+ [Item #1234545] with known titer in Peptone solution was purchased from Carolina Biological Supply. Serial 10:1 dilutions were made with Peptone to reduce the bacteriophage concentration, ultimately by four orders of magnitude. The dilution sequence and the resulting concentrations of Coliphage T4 particles are shown in the Data Appendix. Each dilution was challenged with 0.5 ml of

*E. coli* [Carolina Biological Supply] added to Peptone to produce a standard stock solution which was used in each determination.

The instantaneous presence of an electrochemical response upon the addition of the *E. coli* suspension, was followed by a return to below baseline response over 1 minute in all conditions. A Peptone blank was also run in the same system as a control.

The downward displacement values for the dilution sequence are shown in the Table 3 below.

TABLE 3

| Condition | Downward Displacement [TI Units] |
|---|---|
| Base | 0.105 |
| Dilution 1 | 0.07 |
| Dilution 2 | 0.41 |
| Dilution 3 | 0.28 |
| Dilution 4 | 0.08 |
| Blank | 0.05 |

The use of selective bacteriophages as a means of decontaminating food products from disease causing pathogenic bacteria has been proposed and widely discussed within the industry. To this end, bacteriophages selective for *E. coli* O157, *Salmonella*, and the Shiga Producing Bacterial mixed materials are commercially available.

These reaction of these bacteriophages with liquefied food contamination preparations in either a stationary reaction cell or a flow cell provides a direct passive electrochemical detection method for these contaminants without need for incubation, amplification or complex laboratory procedures.

TABLE 4

| Serial Dilution of the Coliphage T4 | | | | | | | | |
|---|---|---|---|---|---|---|---|---|
| Serial Dilution Experiment Sequence 0.1 Ratio | | | | | | | | |
| | Base Case 1 ml Sample | | First 1 ml Sample | | Second 1 ml Sample | | Third 1 ml Sample | Fourth 1 ml Sample |
| | | Aliquot | | Aliquot | | Aliquot | | Aliquot |
| Vol. of Diluted Phage Sol'n | 0.1 | 0.10 ml | 0.1 | 0.10 ml | 0.1 | 0.10 ml | 0.1 | 0.10 ml | 0.1 |
| Proportion of Phage in Solution | 1 | | 0.066666667 | | 0.004444444 | | 0.000296296 | | 1.97531E−05 |
| Volume of Peptone Diluent | 1 | | 1 | | 1 | | 1 | | 1 |
| Volume of *E. coli* Solution | 0.5 | | 0.5 | | 0.5 | | 0.5 | | 0.5 |
| Concentration Multiplier | 0.66667 | | 0.044444444 | | 0.002962963 | | 0.000197531 | | 1.31687E−05 |
| Base Phage Titer | 7.30E+09 | | 7.30E+09 | | 7.30E+09 | | 7.30E+09 | | 7.30E+09 |
| Diluted Phage Titer (Particles/ml) | 1.10E+10 | | 3.24E+08 | | 2.16E+07 | | 1.44E+06 | | 9.61E+04 |
| Dilution Ratio | 0.1 | | | | | | | | |

Process Note:

Aliquot 0.10 ml of Phage Solution with 1.0 ml of Peptone Broth Diluent

Another embodiment and application of this invention is in the ex vivo testing for allergic and hypersensitivity reactions to outside materials up to and including anaphylactic shock. In this embodiment, the subject individual provides a biological sample of blood, saliva or other material, which is representative of his/her individual immune system. That sample is placed in a test chamber of this invention, and is then challenged with the potential allergen. In an allergically sensitive case, the electrochemical detection of immediate large immune reaction, as an antibody-antigen reaction or large, immediate histamine cascade response, indicates the presence of individual hypersensitivity. This embodiment is particularly useful in screening for drug and environmental allergies, particularly when such allergic reactions can cause permanent injury or death. This testing is quick and specific to the individual.

Those skilled in the art to which this application relates will appreciate that other and further additions, deletions, substitutions and modifications may be made to the described embodiments.

What is claimed is:

1. A bio-sensor device for the electrochemical detection of a bacterial pathogen, the device comprising:

a sample chamber including two passive electrical probes to detect pathogenic antigens in a sample containing the bacterial pathogen, wherein the two passive electrical probes detect a reaction voltage corresponding to an antigen-antibody reaction occurring when the pathogenic antigens come into contact with an antibody specific for pathogenic antigens present in the material in the sample chamber and contacted by the two passive electrical probes; and an electronic data module to detect and process electrical signals from the two passive electrical probes corresponding to an amount of the antigen present in the sample, wherein the reaction voltage is detected at the time of the reaction.

2. The bio-sensor device of claim 1, wherein the bacterial pathogen is methicillin-Resistant *Staphylococcus aureus*.

3. The bio-sensor device of claim 1, wherein the bacterial pathogen is *Clostridium difficile*.

4. The bio-sensor device of claim 1, wherein the bacterial pathogen includes methicillin-Resistant *Staphylococcus aureus* and *Clostridium difficile*.

5. The bio-sensor device of claim 1, wherein the pathogen is detected ex vivo from a patient derived sample, including but not limited to blood, saliva, wound exudates, and stool.

6. The bio-sensor device of claim 1, wherein the pathogen is detected from direct testing of a, swab, or washings from a surface.

7. The bio-sensor device of claim 6, wherein the surface is an epidermis of an organism.

8. The bio-sensor device of claim 6, wherein the surface is a potentially contaminated non-biologic surface including a counter-top or synthetic athletic playing surface.

9. The bio-sensor device of claim 6, wherein the surface is a wound dressing.

10. The bio-sensor device of claim 1, wherein the device is configured as a real-time detection device for detecting the presence of the pathogenic antigens, and the real-time detection device is self-contained and field-applicable, not requiring external equipment or highly trained laboratory personnel.

11. The bio-sensor device of claim 10, wherein the two passive electrical probes of the real-time bio-sensor device are configured to respond to electrochemical antigen-antibody events corresponding to the antigen-antibody reaction within 60 seconds of the sample containing the pathogenic antigens and the antibody-containing reaction medium in the sample chamber becoming in contact with each other.

12. The bio-sensor device of claim 10, wherein the real-time bio-sensor device is configured for direct electrochemical reaction detection of the antigen-antibody reaction.

13. The bio-sensor device of claim 10, wherein the real-time bio-sensor device is not sensitive to detection of reaction products of the antigen-antibody reaction.

14. The bio-sensor device of claim 1, wherein the antibody specific for the pathogenic antigens present in the material in the sample chamber is coated onto one or more of the two passive electrical probes.

15. The bio-sensor device of claim 1, wherein the antibody specific for the pathogenic antigens present in the material in the sample chamber is coated or adsorbed onto a passive filler located within the sample chamber.

16. The bio-sensor device of claim 1, wherein the sample chamber includes a port for introducing a liquid reagent containing the antibody specific for the pathogenic antigens present in the material in the sample chamber.

* * * * *